United States Patent
Itai (10) Patent No.: US 9,585,569 B2
(45) Date of Patent: Mar. 7, 2017

(54) VIRTUAL ENDOSCOPIC PROJECTION IMAGE GENERATING DEVICE, METHOD AND PROGRAM

(71) Applicant: FUJIFILM Corporation, Tokyo (JP)

(72) Inventor: Yoshinori Itai, Tokyo (JP)

(73) Assignee: FUJIFILM CORPORATION, Tokyo (JP)

( * ) Notice: Subject to any disclaimer, the term of this patent is extended or adjusted under 35 U.S.C. 154(b) by 0 days.

(21) Appl. No.: 14/947,966

(22) Filed: Nov. 20, 2015

(65) Prior Publication Data

US 2016/0157726 A1 Jun. 9, 2016

Related U.S. Application Data

(63) Continuation of application No. PCT/JP2014/002747, filed on May 26, 2014.

(30) Foreign Application Priority Data

May 28, 2013 (JP) .................. 2013-111860

(51) Int. Cl.
*G06K 9/00* (2006.01)
*A61B 5/00* (2006.01)
(Continued)

(52) U.S. Cl.
CPC ............ *A61B 5/0084* (2013.01); *A61B 6/461* (2013.01); *A61B 6/5205* (2013.01);
(Continued)

(58) Field of Classification Search
CPC ..... A61B 5/0084; A61B 6/461; A61B 6/5205; A61B 2576/00; G06T 19/003; G06T 2210/41
See application file for complete search history.

(56) References Cited

U.S. PATENT DOCUMENTS 6,346,940 B1  2/2002  Fukunaga
2011/0123077 A1  5/2011  Goto
(Continued)

FOREIGN PATENT DOCUMENTS

JP   H 10-234663 A   9/1998
JP   H 10-234664 A   9/1998
(Continued)

OTHER PUBLICATIONS

International Search Report (ISR) (PCT Form PCT/ISA/210), in PCT/JP2014/002747, dated Sep. 22, 2014.
(Continued)

*Primary Examiner* — Chan Park
*Assistant Examiner* — Timothy Choi
(74) *Attorney, Agent, or Firm* — Mcginn IP Law Group, PLLC.

(57) ABSTRACT

A view point is set inside a hollow organ, a clip plane crossing an internal cavity of the hollow organ is set in a position spaced apart in a visual line direction from the view point, a field of view from the view point is divided into a first field-of-view range in which the inside of the hollow organ is viewed and a second field-of-view range other than the first field-of-view range, a projection image is acquired using a template which is defined so that an inner wall surface of a large intestine is able to be drawn in the first field-of-view range, a projection image is acquired using a template which is defined so that a contact surface with the inner wall surface of the air region of the large intestine is able to be drawn in the second field-of-view range, and the projection images are connected.

10 Claims, 7 Drawing Sheets

(51) Int. Cl.
*G06T 19/00* (2011.01)
*A61B 6/00* (2006.01)
(52) U.S. Cl.
CPC ........ *G06T 19/003* (2013.01); *A61B 2576/00* (2013.01); *G06T 2210/41* (2013.01)

(56) References Cited

U.S. PATENT DOCUMENTS

| | | | |
|---|---|---|---|
| 2013/0023730 A1* | 1/2013 | Kitamura | A61B 1/00009 600/104 |
| 2013/0039560 A1 | 2/2013 | Goto | |
| 2013/0137926 A1* | 5/2013 | Itai | A61B 1/0005 600/111 |
| 2015/0287243 A1* | 10/2015 | Itai | G06T 19/003 345/419 |
| 2016/0086371 A1* | 3/2016 | Itai | G06T 15/08 382/131 |

FOREIGN PATENT DOCUMENTS

| | | |
|---|---|---|
| JP | 2007-531554 A | 11/2007 |
| JP | 2007-537771 A | 12/2007 |
| JP | 2010-017490 A | 1/2010 |
| WO | WO 2011/142222 A1 | 11/2011 |

OTHER PUBLICATIONS

International Search Opinion (PCT/ISA/237) and an English translation.

* cited by examiner

VIRTUAL ENDOSCOPIC PROJECTION IMAGE GENERATING DEVICE, METHOD AND PROGRAM

CROSS-REFERENCE TO RELATED APPLICATIONS

This application is a Continuation of PCT International Application No. PCT/JP2014/002747 filed on May 26, 2014, which claims priority under 35 U.S.C. §119 (a) to Japanese Patent Application No. 2013-111860 filed on May 28, 2013. Each of the above application(s) is hereby expressly incorporated by reference, in its entirety, into the present application.

BACKGROUND OF THE INVENTION

Field of the Invention

The present invention relates to a projection image generating device, method and program that generate a projection image from volume data representing a three-dimensional region including a hollow organ.

Description of the Related Art

In the medical field, volume data (three-dimensional image data) obtained by photographing a patient is converted into an image suitable for observation and displayed. In particular, a virtual endoscopic image is widely used for observation of a hollow organ such as a large intestine or a bronchus.

However, in the virtual endoscopic image, there may be a portion in which a visual line is blocked by a front wall or the like and does not appear on the image. For example, when there are a large number of folds on an inner wall of the large intestine and the view point exists on a side surface of any of the folds, there is a problem in that a lesion (e.g., polyp) on a back surface of the fold does not appear on the image and cannot be observed.

On the other hand, a scheme in which a view point is placed inside a hollow organ and the hollow organ is drawn as a mesh or a translucent organ such that an image in which a back wall blocked by a front wall of the hollow organ and not visible has been drawn is displayed to be superimposed on an image in which the front wall of the hollow organ has been drawn has been proposed in JP1998-234663A (JP-H10-234663A). A scheme in which a projection image generated by placing a view point outside a hollow organ is displayed side by side with a virtual endoscopic image generated by placing the view point inside the hollow organ, or switched to the virtual endoscopic image and displayed such that the hollow organ can be observed from various view points has been proposed in JP2007-537771A.

SUMMARY OF THE INVENTION

However, the scheme proposed in JP1998-234663A (JP-H10-234663A) has a problem in that images of a plurality of wall surfaces appear in an overlapping manner, and thus, it is difficult to observe surface shapes of the wall surfaces. Further, the scheme proposed in JP2007-537771A has a problem that the number of images to be confirmed increases and more time is taken due to image confirmation work.

The present invention has been made in view of the above circumstances, and an object of the prevent invention is to provide a projection image generating device, method and program that provide a projection image of a hollow organ in which a portion that does not appear on a normal virtual endoscopic image of the hollow organ due to a visual line being blocked by a wall in the normal virtual endoscopic image is partially drawn so that a surface shape thereof can be easily observed, in addition to a portion that can be observed in the normal virtual endoscopic image of the hollow organ.

A first projection image generating device according to the present invention includes condition setting means that sets a view point inside a hollow organ and sets a visual line direction from the view point in volume data representing a three-dimensional region including the hollow organ; clip plane setting means that sets a clip plane crossing an internal cavity of the hollow organ in a position spaced apart in the visual line direction from the view point; dividing means that sets a portion distant relative to the clip plane from the view point of the three-dimensional region as a visible region, and divides a field of view from the view point into a first field-of-view range in which the inside of the hollow organ is viewed and a second field-of-view range other than the first field-of-view range; and projection image generation means that projects a portion within the first field-of-view range of the visible region onto a projection plane set corresponding to the view point using a first template in which a relationship between a data value and opacity is defined so that an inner wall surface of the hollow organ is able to be drawn, to thereby acquire a first projection image in the first field-of-view range, projects a portion within the second field-of-view range of the visible region onto the projection plane using a second template in which the relationship between the data value and the opacity is defined so that a contact surface with the inner wall surface of the air region in the hollow organ is able to be drawn, to thereby acquire a second projection image in the second field-of-view range, and generates a projection image in the entire field of view in which the first projection image is connected to the second projection image.

Here, the "hollow organ" refers to an organ having a tubular or bag form, and includes a stomach, a large intestine, a rectum, a bronchus, a bladder, a blood vessel, or the like. The same applies to the following.

In the first projection image generating device, the division means may set a plurality of visual lines extending through the clip plane from the view point in the field of view, may determine, for each visual line, whether there is a wall of the hollow organ between the view point and a point crossing the clip plane, may set a portion including the visual line in which it is determined that there is a wall in the field of view as the first field-of-view range, and may set a portion including the visual line in which it is determined that there is no wall as the second field-of-view range.

Further, the clip plane setting means may set a plane passing through a point separated by a predetermined distance in the visual line direction from the view point, as the clip plane, or may set a curved surface centered on the view point as the clip plane.

Further, the first template may be a template in which opacity indicating a transparent state is allocated to a data value of the air region and opacity indicating an opaque state is allocated to a data value of an inner wall surface region of the hollow organ, and the second template may be a template in which the opacity indicating an opaque state is allocated to a data value of the air region and the opacity indicating a transparent state is allocated to a data value of a region other than the air region in the field of view.

Further, a second projection image generating device according to the present invention includes condition setting means that sets a projection plane crossing an internal cavity of a hollow organ and sets a visual line direction perpendicular to the projection plane in volume data representing a three-dimensional region including the hollow organ; clip plane setting means that sets a clip plane crossing an internal cavity of the hollow organ; dividing means that sets a portion in front in the visual line direction relative to the clip plane of the three-dimensional region as a visible region, and divides the field of view from the projection plane into a first field-of-view range in which the inside of the hollow organ is viewed and a second field-of-view range other than the first field-of-view range; and projection image generation means that projects a portion within the first field-of-view range of the visible region onto the projection plane using a first color template in which a relationship between a data value and opacity is defined so that an inner wall surface of the hollow organ is able to be drawn, to thereby acquire a first projection image in the first field-of-view range, projects a portion within the second field-of-view range of the visible region onto the projection plane using a second color template in which the relationship between the data value and the opacity is defined so that a contact surface with the inner wall surface of the air region in the hollow organ is able to be drawn, to thereby acquire a second projection image in the second field-of-view range, and generates a projection image in the entire field of view in which the first projection image is connected to the second projection image.

Each of first and second projection image generating methods according to the present invention is a method of causing one or a plurality of computers or one or a plurality of computer processors such as CPUs to execute each means of the first and second projection image generating devices.

Each of first and second projection image generating programs according to the present invention is a program for causing one or a plurality of computers to function as each means of the first and second projection image generating devices. These programs are recorded on a recording medium such as a CD-ROM or a DVD, or recorded in a storage attached to a server computer or a network storage so that the programs can be downloaded, and provided to a user.

According to the first and second projection image generating devices, methods and programs of the present invention, it is possible to provide a projection image for a hollow organ in which a portion that does not appear on the normal virtual endoscopic image of the hollow organ due to a visual line being blocked by a wall in the normal virtual endoscopic image is partially drawn so that the surface shape thereof can be easily observed, in addition to a portion that can be observed in the normal virtual endoscopic image of the hollow organ, and accordingly, to improve observation performance for an observer.

DESCRIPTION OF THE PREFERRED EMBODIMENTS

Figure 1:
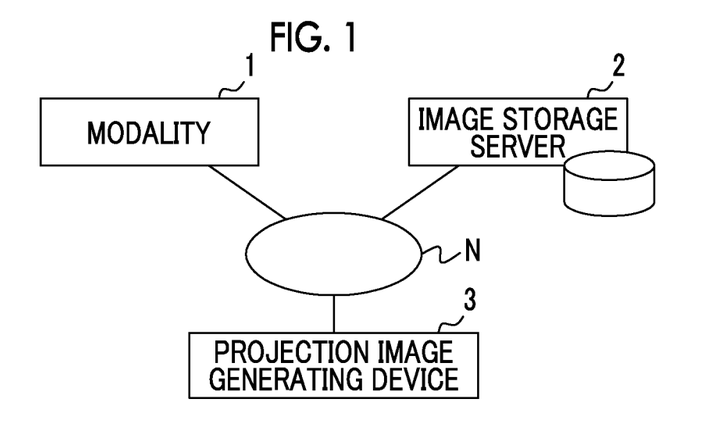
FIG. 1 is a schematic configuration diagram of an image diagnosis support system to which a projection image generating device of the present invention is introduced.

Hereinafter, an image diagnosis support system to which a projection image generating device according to an embodiment of the present invention is introduced will be described. FIG. 1 is a hardware configuration diagram illustrating an overview of the image diagnosis support system. As illustrated in FIG. 1, in this system, a modality 1, an image storage server 2, and a projection image generating device 3 are connected in a state in which the modality 1, the image storage server 2, and the projection image generating device 3 can communicate over a network N.

The modality 1 is an apparatus that photographs an inspection target portion of a subject, generates volume data (3D image data) indicating the portion, adds supplementary information defined according to a standard such as digital imaging and communications in medicine (DICOM) to the volume data, and outputs the resultant volume data. Specific examples thereof may include a computed tomography (CT) apparatus, and a magnetic resonance imaging (MRI) apparatus.

The image storage server 2 is a computer that stores the volume data acquired by the modality 1 or the like in a database and manages the volume data. The image storage server 2 includes a large-capacity external storage device or database management software (for example, object relational database (ORDB) management software).

The projection image generating device 3 is a computer that includes a central processing unit (CPU) and a semiconductor memory, or a storage such as a hard disk or a solid state drive (SSD) in which the projection image generating program of the present embodiment has been installed. The projection image generating program defines, as processes executed by the CPU in the computer, an organ region extraction process, a condition setting process, a clip plane setting process, a dividing process, a projection image generation process, and the like. An input device such as a mouse or a keyboard, and a display device such as a display are connected to the projection image generating device 3.

Figure 2:
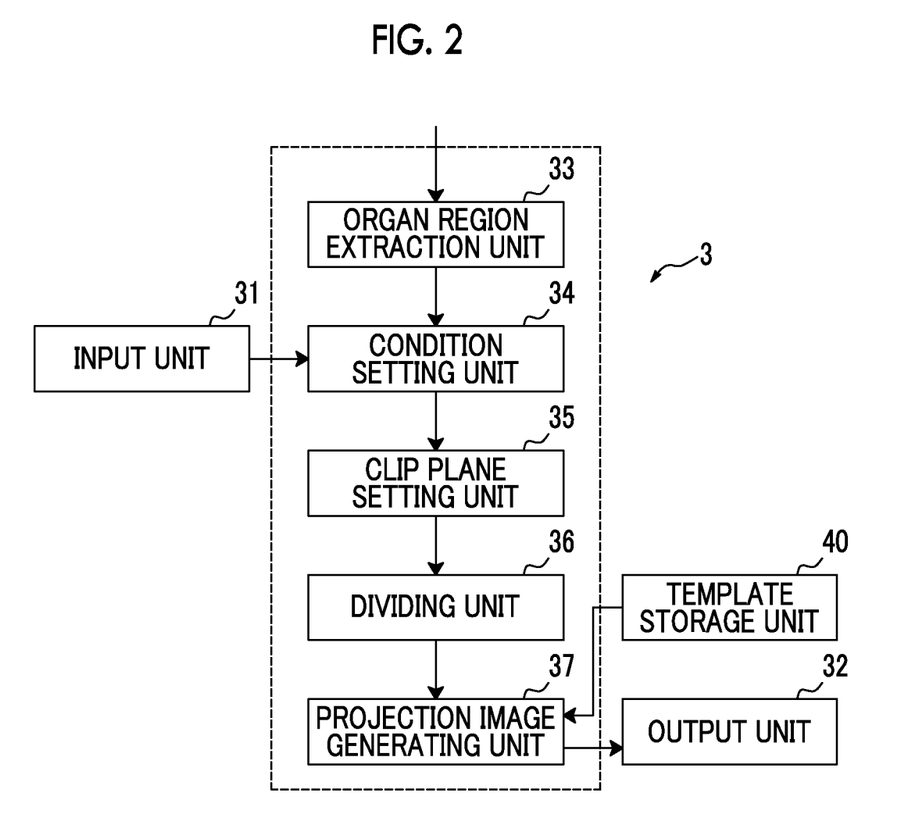
FIG. 2 is a functional block diagram of a projection image generating device in the present embodiment.

FIG. 2 is a block diagram in which the projection image generating device 3 is divided at a function level. As illustrated in FIG. 2, the projection image generating device 3 includes an organ region extraction unit 33, a condition setting unit 34, a clip plane setting unit 35, a dividing unit 36, a projection image generating unit 37, an input unit 31, an output unit 32, and a template storage unit 40. A function of each processing unit in a dashed box is realized by the CPU executing a surgery support program, the input unit 31 is realized by the input device, the output unit 32 is realized by the output device, and the template storage unit 40 is realized by the storage.

The organ region extraction unit 33 receives the volume data representing a three-dimensional region including a hollow organ of a target acquired from the modality 1, the image storage server 2, or the like, and extracts a region of the hollow organ. Examples of the hollow organ include a stomach, a large intestine, a rectum, a bronchus, a bladder, and a blood vessel. In this embodiment, a large intestine region is assumed to be extracted. In a method of extracting the large intestine region from the volume data, specifically, a threshold value determination is first performed on the volume data so as to extract a region estimated as an air region. Through this process, a region of a hollow organ (for example, a large intestine, a small intestine, or a duodenum) of an abdomen is detected as a candidate region of the large intestine. Subsequently, features of the large intestine are detected from each candidate region, and a region from which the largest number of features are detected is determined to be the large intestine region.

The condition setting unit 34 receives the hollow organ region extracted by the organ region extraction unit 33, sets a view point 4 inside the hollow organ, and sets a visual line direction 5 from the view point 4. Here, the inside of the hollow organ means a space more inside a wall of the hollow organ. In the example illustrated in FIG. 3, an air region 12 more inside a wall region 11 of the large intestine corresponds to inside the hollow organ. Here, for ease of understanding, description will be given with reference to the drawings in which a three-dimensional space of the volume data is two-dimensionally schematized.

Figure 3:
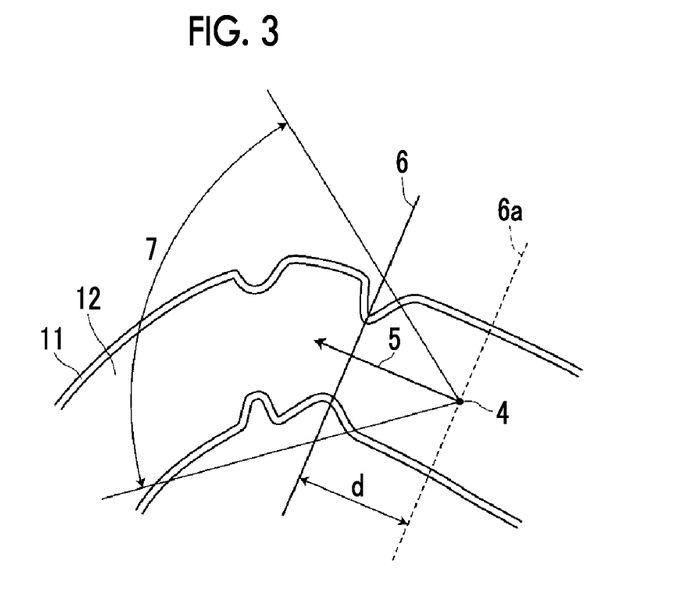
FIG. 3 is a diagram illustrating a process of setting a view point or a visual line direction and a clip plane.

Specifically, the condition setting unit 34 sets the view point 4 in an initial position (or any other position) on a core line extracted from the large intestine region through a thinning process, and sets a forward or depth direction of the core line from the position as a visual line direction 5. Alternatively, the condition setting unit 34 receives an arbitrary designated position and an arbitrary designated direction inside the large intestine in a two-dimensional sectional image or a three-dimensional image of the large intestine or the like displayed on the screen from the user, and sets the designated position and the designated direction as the view point 4 and the visual line direction 5, respectively. Accordingly, the view point 4 and the visual line direction 5 as illustrated in FIG. 3 are set. Further, by setting the view point 4 and the visual line direction 5, a predetermined range in a viewing angle centered on the visual line direction 5 is set as a field of view 7 from the view point 4.

Figure 4:
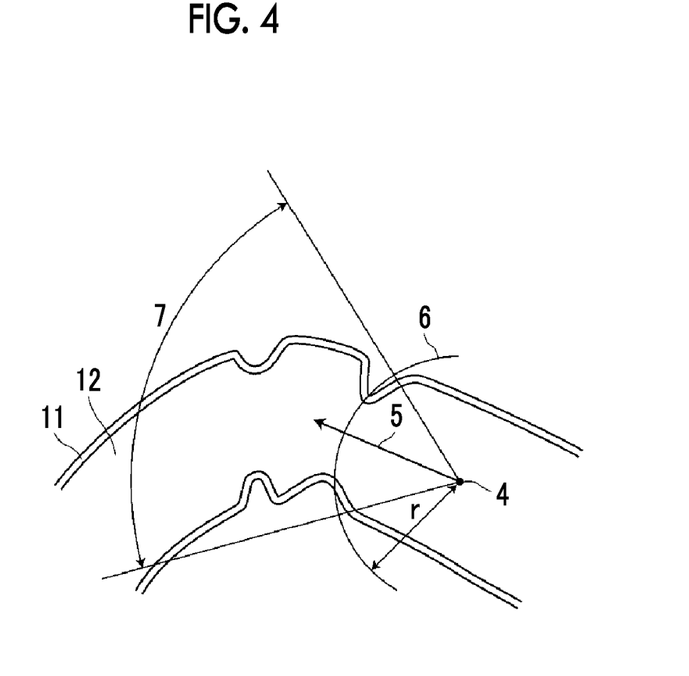
FIG. 4 is a diagram illustrating a process of setting the clip plane.

The clip plane setting unit 35 sets a clip plane 6 crossing an internal cavity of the hollow organ in a position spaced apart in the visual line direction 5 from the view point 4 set by the condition setting unit 34. Specifically, as illustrated in FIG. 3, the clip plane setting unit 35 sets a plane separated by a predetermined distance d from a plane 6a passing through the view point 4 and being perpendicular to the visual line direction 5 as a clip plane 6. Alternatively, as illustrated in FIG. 4, the clip plane setting unit 35 sets a curved surface having a radius r centered on the view point 4 as the clip plane 6. In this case, a magnitude of the distance d or the radius r may be appropriately set in consideration of, for example, a ratio of the inside of the hollow organ to be represented on the projection image generated by a projection image generation section 37 to the other region.

Figure 5:
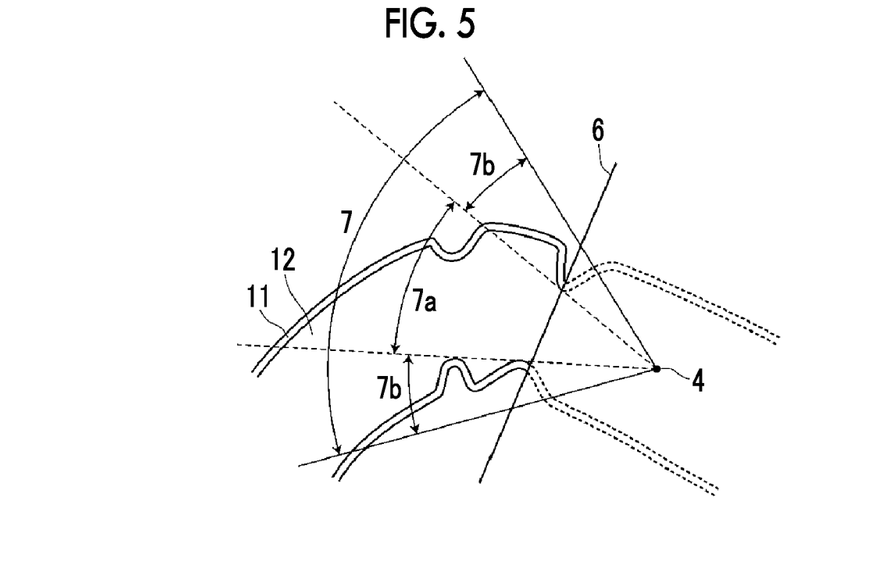
FIG. 5 is a diagram illustrating a process of dividing a field of view.
Figure 6:
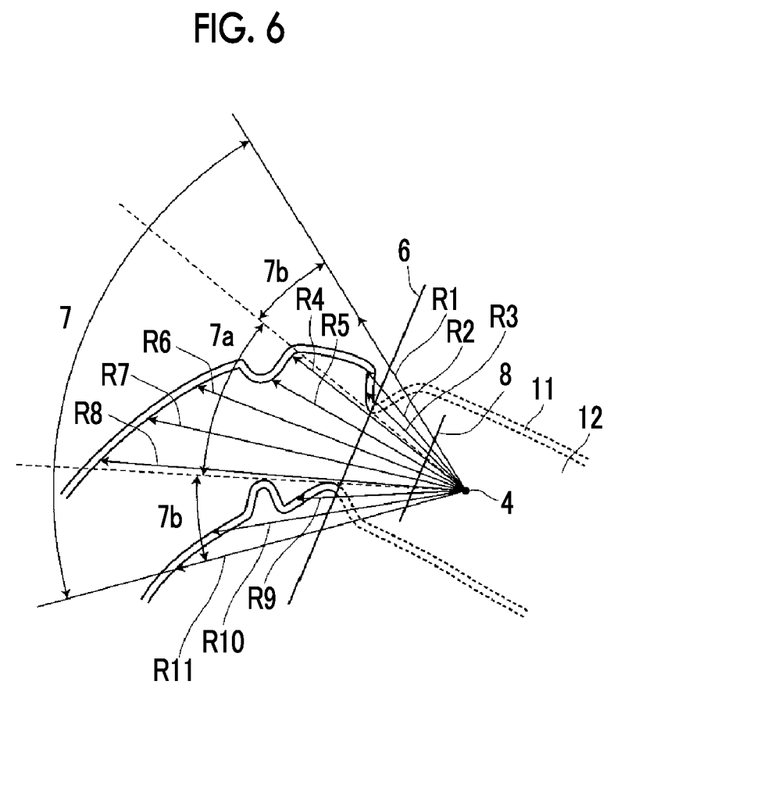
FIG. 6 is a diagram illustrating the process of dividing the field of view.

The dividing unit 36 sets a portion distant relative to the clip plane 6 from the view point 4 of the three-dimensional region as a visible region, and divides the field of view 7 from the view point 4 into a first field-of-view range 7a in which the inside of the hollow organ is viewed and a second field-of-view range 7b other than the first field-of-view range 7a, as illustrated in FIG. 5. Specifically, as illustrated in FIG. 6, the dividing unit 36 sets a plurality of visual lines R1 to R11 extending through the clip plane 6 from the view point 4 in the field of view 7, determines, for each visual line, whether or not the wall region 11 of the large intestine is present from the view point 4 to a point crossing the clip plane 6, sets a portion including the visual lines R4 to R8 in which it is determined that there is no wall region 11 as a first field-of-view range 7a, and sets respective portions including the visual lines R1 to R3 and R9 to R11 in which it is determined that there is the wall region 11 as a second field-of-view range 7b.

In this case, the determination as to whether or not there is the wall region 11 in a section from the view point 4 of each visual line to the point crossing the clip plane 6 can be performed based on a data value of a voxel in the same section. For example, an opacity is allocated to each voxel in advance, and the opacities of the voxels are cumulatively summed along the visual line. It can be determined that there is the wall region 11 when a cumulative value reaches a predetermined upper threshold value in the same section, and it can be determined that there is no wall region 11 when the cumulative value does not reach the upper threshold value. Alternatively, it is also possible to perform the above determination based on whether or not a voxel having a data value corresponding to the wall region 11 of the large intestine in the same section.

The projection image generating unit 37 allocates a color or opacity corresponding to the data value to each voxel of the visible region by referring to a color template in which a relationship between the data value and color or opacity is defined, sets the plurality of visual lines from the view point 4 in the field of view 7, and projects the visible region onto a projection plane 8 set perpendicular to the visual line direction 5 along each visual line to generate a projection image from the view point 4.

Figure 7:
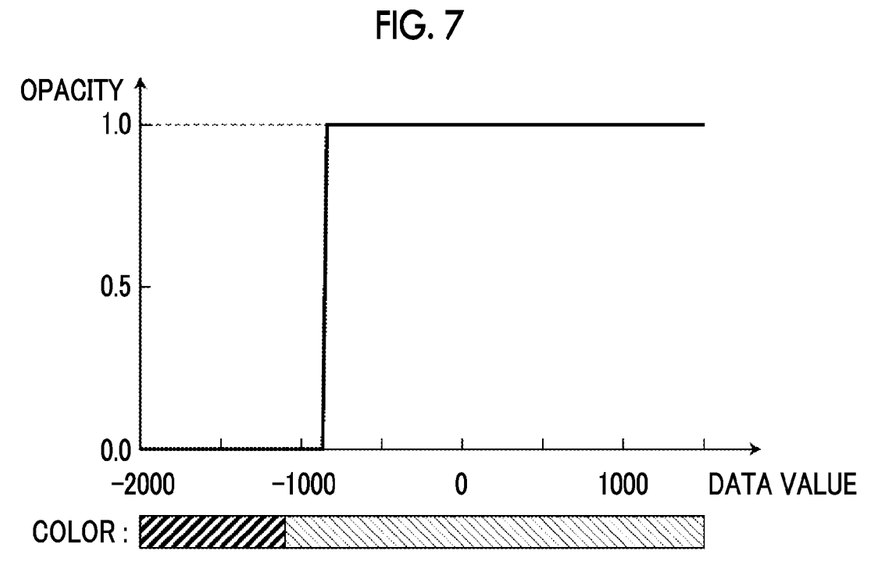
FIG. 7 is a diagram illustrating an example of a color template defined so that an inner wall surface of a large intestine can be drawn.
Figure 8:
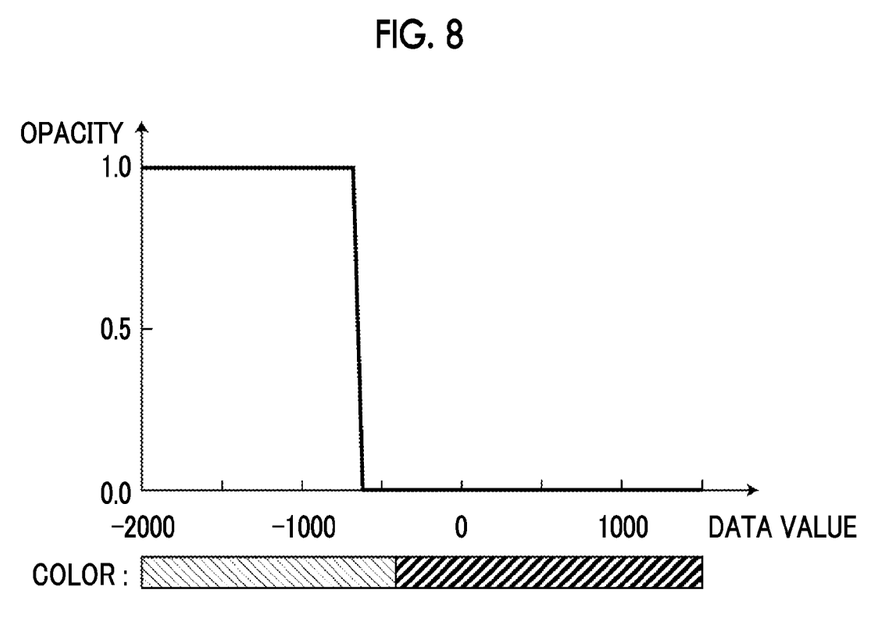
FIG. 8 is a diagram illustrating an example of a color template defined so that a contact surface with an inner wall surface of an air region in the large intestine can be drawn.

In particular, the projection image generating unit 37 projects a portion within the first field-of-view range 7a of the visible region onto the projection plane 8 using a first color template in which opacity (0%) indicating a transparent state is allocated to a data value of the air region, opacity (100%) indicating an opaque state is allocated to a data value of the inner wall surface region of the large intestine, and a relationship between a data value and opacity is defined so that the inner wall surface of the large intestine can be drawn, as illustrated in, for example, FIG. 7, to thereby acquire the first projection image in the first field-of-view range 7a, projects a portion within the second field-of-view range 7b of the visible region onto the projection plane 8 using a second color template in which opacity (100%) indicating an opaque state is allocated to a data value of the air region, opacity (0%) indicating a transparent state is allocated to a data value of a region other than the air region within the field of view 7, and the relationship between the data value and the opacity is defined so that a contact surface with the inner wall surface of the air region in the large intestine can be drawn, as illustrated in, for example, FIG. 8, to thereby acquire the second projection image in the second field-of-view range 7b, and generates the projection image in the entire field of view 7 in which the first projection image is connected to the second projection image. It is assumed that the first and second color templates have been stored in the template storage unit 40 in advance so that the first and second templates can be referred to.

Figure 9:
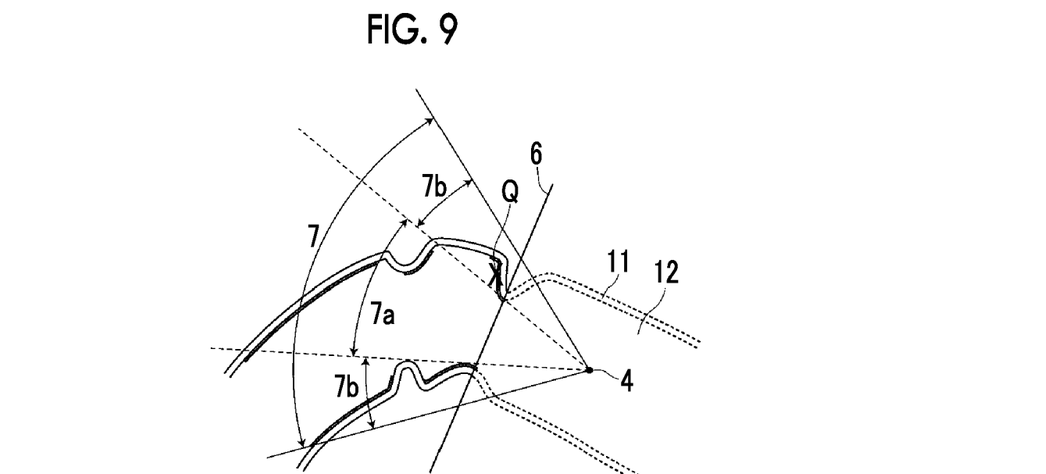
FIG. 9 is a diagram illustrating a drawing range of a projection image according to the present invention.
Figure 10:
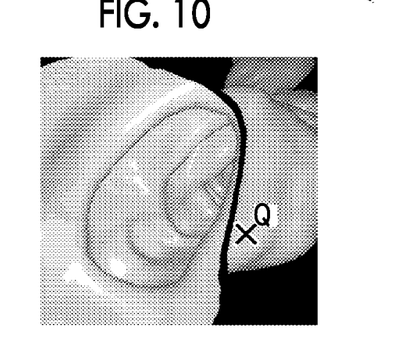
FIG. 10 is a diagram of an example of the projection image according to the present invention.
Figure 11:
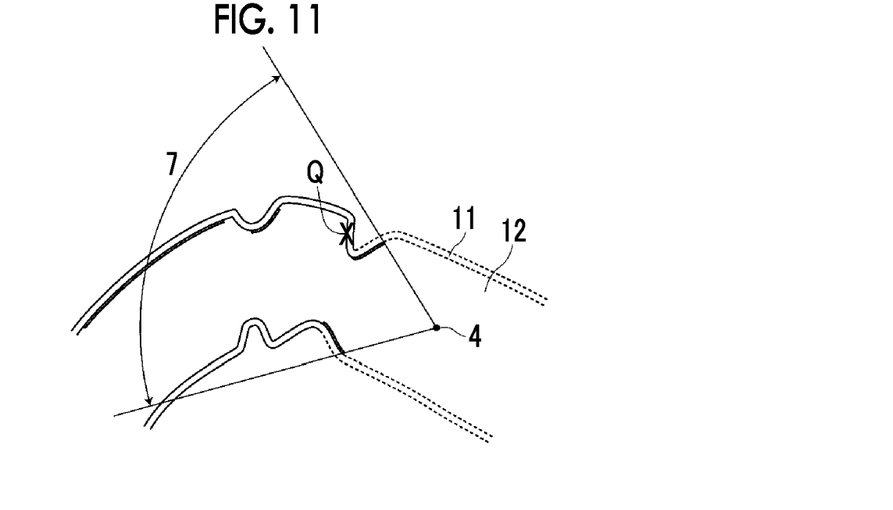
FIG. 11 is a diagram illustrating a drawing range of a conventional virtual endoscopic image.
Figure 12:
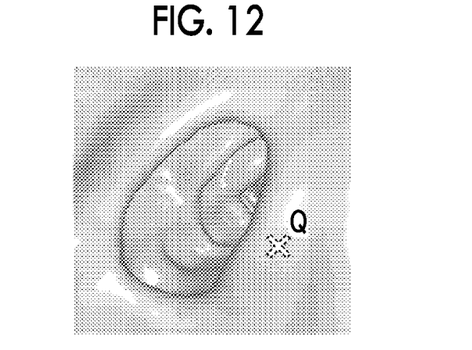
FIG. 12 is a diagram illustrating an example of the conventional virtual endoscopic image.

Thus, a projection image of the large intestine in which a contact surface (a surface having substantially the same shape as that of the inner wall surface having a concavo-convex pattern reverse to a concavo-convex pattern of the inner wall surface) between an inner wall surface of the large intestine within the first field-of-view range 7a and an inner wall surface of the air region 12 in the large intestine in the second field-of-view range 7b as indicated by a bold line in FIG. 9 is drawn is generated. FIG. 10 is a view illustrating an example of the projection image generated by the projection image generating unit 37. On the other hand, in a conventional virtual endoscopic image, only an inner wall surface of a portion at which the visual line directly arrives as indicated by a bold line in FIG. 11 is a drawing target, and accordingly, a projection image as illustrated in FIG. 12 is obtained under conditions of the same view point and the same visual line direction as those in FIG. 10. As illustrated in FIG. 11, in the conventional virtual endoscopic image, a back surface region Q of a fold indicated by a mark x does not appear on the image due to the visual line being blocked by the wall, whereas in the projection image according to the present invention, that portion is also drawn as illustrated in FIG. 9. Further, in the projection image according to the present invention illustrated in FIG. 10, a back surface region Q (indicated by a dotted mark x) of the fold that does not appear on the image due to the visual line being blocked by the wall in the virtual endoscopic image illustrated in FIG. 12 is drawn such that a surface shape thereof can be easily observed.

As described above, according to the projection image generating device 3 of the present embodiment, it is possible to provide the projection image of the hollow organ in which a portion that does not appear on the normal virtual endoscopic image of the hollow organ due to the visual line being blocked by the wall in the normal virtual endoscopic image is partially drawn so that the surface shape thereof can be easily observed, in addition to the portion that can be observed in the normal virtual endoscopic image of the hollow organ, and accordingly, to improve observation performance for an observer.

While in the above embodiment, the case in which the projection image is generated through perspective projection has been described, the projection image exhibiting substantially the same effects can be generated through parallel projection. Hereinafter, an embodiment in which the projection image is generated through parallel projection, as another embodiment of the present invention, will be described. Since a portion other than a portion that will be described below is the same as that when the projection image is generated through the perspective projection, a description thereof will be omitted.

Figure 13:
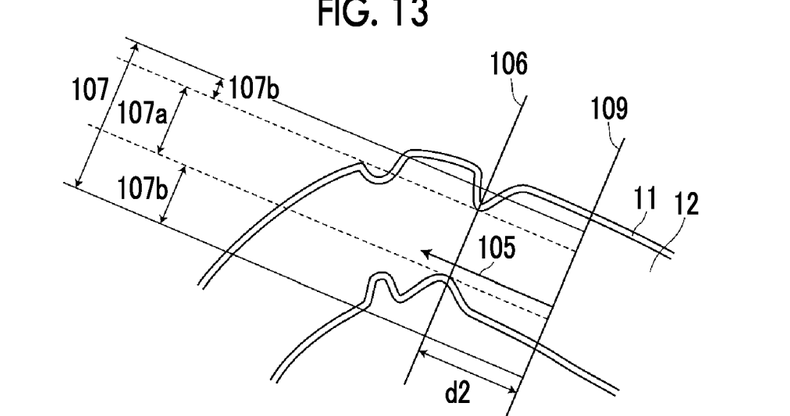
FIG. 13 is a diagram illustrating a process of generating a projection image through parallel projection.

The condition setting unit 34 of the present embodiment sets a projection plane 109 crossing an internal cavity of a hollow organ and sets a visual line direction 105 perpendicular to the projection plane 109 in volume data representing a three-dimensional region including the hollow organ, as illustrated in FIG. 13. Specifically, the condition setting unit 34 sets a plane perpendicular to a core line in an initial position (or any other position) of the core line extracted from the large intestine region through a thinning process as a projection plane 109, and sets a forward or depth direction of the core line from the position as a visual line direction 105. Alternatively, the condition setting unit 34 receives a designation of a plane and a direction crossing the internal cavity of the hollow organ in a two-dimensional sectional image, a three-dimensional image, or the like of the large intestine displayed on the screen from the user, and sets the designated plane and the direction as the projection plane 109 and the visual line direction 105, respectively. Further, the condition setting unit 34 sets a field of view 107 from the projection plane 109 in which both of the inside and the outside of the hollow organ are viewed. The clip plane setting unit 35 sets a clip plane 106 crossing the internal cavity of the hollow organ. Specifically, a plane separated by a predetermined distance d2 from the projection plane 109 is set as the clip plane 106.

Figure 14:
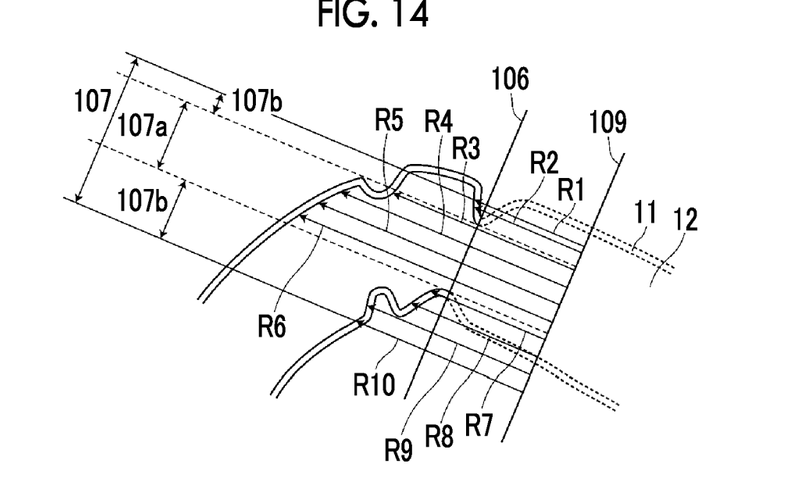
FIG. 14 is a diagram illustrating a process of dividing the field of view.

Further, the dividing unit 36 of this embodiment sets a portion in front in the visual line direction 105 from the clip plane 106 of the three-dimensional region as a visible region, and divides a field of view from the projection plane 109 into a first field-of-view range 107a in which the inside of the hollow organ is viewed, and a second field-of-view range 107b other than the first field-of-view range 107a. Specifically, as illustrated in FIG. 14, a plurality of visual lines R1 to R10 extending through the clip plane 106 from the projection plane 109 are set in the field of view 107, it is determined, for the respective visual lines R1 to R8 of which start points exist inside the hollow organ, whether or not there is the wall region 11 of the large intestine between the start point and a point crossing the clip plane 106, a portion including the visual lines R3 to R6 in which it is determined that there is no wall region 11 is defined as the first field-of-view range 107a, and each of a portion including the visual lines R1, R2, R7, and R8 in which it is determined that there is the wall region 11 and a portion including the visual lines R9 and R10 of which the start points exist outside the hollow organ is defined as the second field-of-view range 107b.

Figure 15:
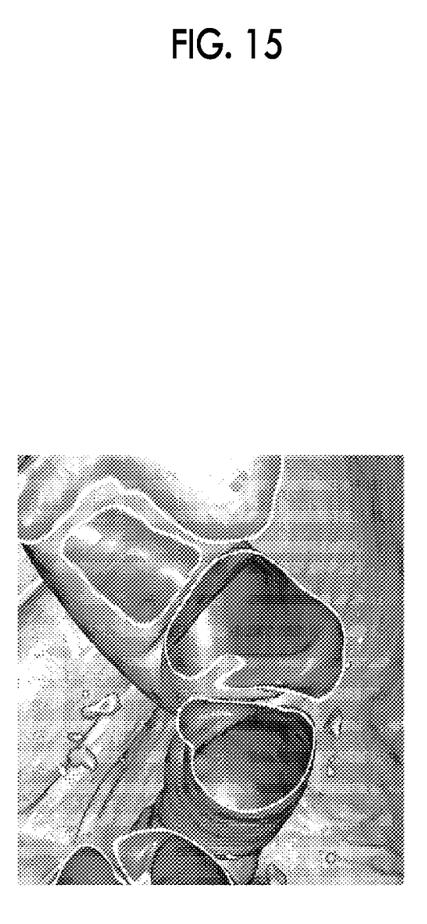
FIG. 15 is a diagram illustrating an example of a projection image generated through parallel projection.

The projection image generating unit 37 projects a portion within the first field-of-view range 107a of the visible region onto the projection plane 109 using the first color template in which a relationship between a data value and opacity is defined so that the inner wall surface of the large intestine can be drawn, to thereby acquire the first projection image in the first field-of-view range 107a, projects a portion within the second field-of-view range 107b of the visible region onto the projection plane 109 using the second color template in which the relationship between the data value and the opacity is defined so that a contact surface with the inner wall surface of the air region in the large intestine can be drawn, to thereby acquire the second projection image in the second field-of-view range 107b, and generates the projection image in the entire field of view 107 in which the first projection image is connected to the second projection image. FIG. 15 is a view illustrating an example of the projection image generated by the projection image generating unit 37 of the present embodiment.

Thus, according to the projection image generating device 3 of the present embodiment, it is also possible to provide the projection image of the hollow organ in which a portion that does not appear on the normal virtual endoscopic image of the hollow organ due to the visual line being blocked by the wall in the normal virtual endoscopic image is partially drawn so that the surface shape thereof can be easily observed, in addition to the portion that can be observed in the normal virtual endoscopic image of the hollow organ, and accordingly, to improve observation performance for an observer.

In each embodiment described above, while the case in which the projection image generating device 3 includes the organ region extraction unit 33 has been described, a configuration thereof is not necessarily required and may be provided, when necessary.

What is claimed is:

1. A projection image generating device, comprising:
   a condition setting section that sets a view point inside a hollow organ and sets a visual line direction from the view point in volume data representing a three-dimensional region including the hollow organ;
   a clip plane setting section that sets a clip plane crossing an internal cavity of the hollow organ in a position spaced apart in the visual line direction from the view point;
   a dividing section that sets a portion of the three-dimensional region that is on a distant side of the clip plane from the view point of the three-dimensional region as a visible region, and divides a field of view from the view point into a first field-of-view range in which the inside of the hollow organ is viewed and a second field-of-view range other than the first field-of-view range; and
   a projection image generation section that projects a portion within the first field-of-view range of the visible region onto a projection plane set corresponding to the view point using a first template in which a relationship between a data value and opacity is defined so that an inner wall surface of the hollow organ is able to be drawn, to thereby acquire a first projection image in the first field-of-view range, projects a portion within the second field-of-view range of the visible region onto the projection plane using a second template in which the relationship between the data value and the opacity is defined so that a contact surface with the inner wall surface of the air region in the hollow organ is able to be drawn, to thereby acquire a second projection image in the second field-of-view range, and generates a projection image in the entire field of view in which the first projection image is connected to the second projection image.

2. The projection image generating device according to claim 1,
   wherein the division section sets a plurality of visual lines extending through the clip plane from the view point in the field of view, determines, for each visual line, whether there is a wall of the hollow organ between the view point and a point crossing the clip plane, sets a portion including the visual line in which it is determined that there is a wall in the field of view as the first field-of-view range, and sets a portion including the visual line in which it is determined that there is no wall as the second field-of-view range.

3. The projection image generating device according to claim 1,
   wherein the clip plane setting section sets a plane passing through a point separated by a predetermined distance in the visual line direction from the view point, as the clip plane.

4. The projection image generating device according to claim 1,
   wherein the clip plane setting section sets a curved surface centered on the view point as the clip plane.

5. The projection image generating device according to claim 1,
   wherein the first template comprises a template in which opacity indicating a transparent state is allocated to a data value of the air region and opacity indicating an opaque state is allocated to a data value of an inner wall surface region of the hollow organ, and
   the second template comprises a template in which the opacity indicating an opaque state is allocated to the data value of the air region and the opacity indicating a transparent state is allocated to a data value of a region other than the air region in the field of view.

6. A projection image generating device, comprising:
   a condition setting section that sets a projection plane crossing an internal cavity of a hollow organ and sets a visual line direction perpendicular to the projection plane in volume data representing a three-dimensional region including the hollow organ;
   a clip plane setting section that sets a clip plane crossing an internal cavity of the hollow organ;
   a dividing section that sets a portion in front in the visual line direction relative to the clip plane of the three-dimensional region as a visible region, and divides the field of view from the projection plane into a first field-of-view range in which the inside of the hollow organ is viewed and a second field-of-view range other than the first field-of-view range; and
   a projection image generation section that projects a portion within the first field-of-view range of the visible region onto the projection plane using a first template in which a relationship between a data value and opacity is defined so that an inner wall surface of the hollow organ is able to be drawn, to thereby acquire a first projection image in the first field-of-view range, projects a portion within the second field-of-view range of the visible region onto the projection plane using a second template in which the relationship between the data value and the opacity is defined so that a contact surface with the inner wall surface of the air region in the hollow organ is able to be drawn, to thereby acquire a second projection image in the second field-of-view range, and generates a projection image in the entire field of view in which the first projection image is connected to the second projection image.

7. A projection image generating method, causing one or a plurality of computers to execute:
   a condition setting process of setting a view point inside a hollow organ and setting a visual line direction from the view point in volume data representing a three-dimensional region including the hollow organ;
   a clip plane setting process of setting a clip plane crossing the internal cavity of the hollow organ in a position spaced apart in the visual line direction from the view point;
   a dividing process of setting a portion of the three-dimensional region that is on a distant side of the clip plane from the view point of the three-dimensional region as a visible region, and dividing the field of view from the view point into a first field-of-view range in which the inside of the hollow organ is viewed and a second field-of-view range other than the first field-of-view range; and
   a projection image generation process of projecting a portion within the first field-of-view range of the visible region onto a projection plane set corresponding to the view point using a first template in which a relationship between a data value and opacity is defined so that an inner wall surface of the hollow organ is able to be drawn, to thereby acquire a first projection image in the first field-of-view range, projecting a portion within the second field-of-view range of the visible region onto the projection plane using a second template in which the relationship between the data value and the opacity is defined so that a contact surface with the inner wall surface of the air region of the hollow organ is able to be drawn, to thereby acquire a second projection image in the second field-of-view range, and generating a projection image in the entire field of view in which the first projection image is connected to the second projection image.

8. A projection image generating method, causing one or a plurality of computers to execute:
   a condition setting process of setting a projection plane crossing an internal cavity of a hollow organ and setting a visual line direction perpendicular to the projection plane in volume data representing a three-dimensional region including the hollow organ;
   a clip plane setting process of setting a clip plane crossing the internal cavity of the hollow organ;
   a dividing process of setting a portion in front in the visual line direction relative to the clip plane of the three-dimensional region as a visible region, and dividing the field of view from the projection plane into a first field-of-view range in which the inside of the hollow organ is viewed and a second field-of-view range other than the first field-of-view range; and
   a projection image generation process of projecting a portion within the first field-of-view range of the visible region onto the projection plane using a first template in which a relationship between a data value and opacity is defined so that an inner wall surface of the hollow organ is able to be drawn, to thereby acquire a first projection image in the first field-of-view range, projecting a portion within the second field-of-view range of the visible region onto the projection plane using a second template in which the relationship between the data value and the opacity is defined so that a contact surface with the inner wall surface of the air region in the hollow organ is able to be drawn, to thereby acquire a second projection image in the second field-of-view range, and generating a projection image in the entire field of view in which the first projection image is connected to the second projection image.

9. A non-transitory computer-readable recording medium recording projection image generating program, the program causing a computer to function as:
   a condition setting section that sets a view point inside a hollow organ and sets a visual line direction from the view point in volume data representing a three-dimensional region including the hollow organ;
   a clip plane setting section that sets a clip plane crossing an internal cavity of the hollow organ in a position spaced apart in the visual line direction from the view point;
   a dividing section that sets a portion of the three-dimensional region that is on a distant side of the clip plane from the view point of the three-dimensional region as a visible region, and divides a field of view from the view point into a first field-of-view range in which the inside of the hollow organ is viewed and a second field-of-view range other than the first field-of-view range; and
   a projection image generation section that projects a portion within the first field-of-view range of the visible region onto a projection plane set corresponding to the view point using a first template in which a relationship between a data value and opacity is defined so that an inner wall surface of the hollow organ is able to be drawn, to thereby acquire a first projection image in the first field-of-view range, projects a portion within the second field-of-view range of the visible region onto the projection plane using a second template in which the relationship between the data value and the opacity is defined so that a contact surface with the inner wall surface of the air region in the hollow organ is able to be drawn, to thereby acquire a second projection image in the second field-of-view range, and generates a projection image in the entire field of view in which the first projection image is connected to the second projection image.

10. A non-transitory computer-readable recording medium recording projection image generating program, the program causing a computer to function as:
    a condition setting section that sets a projection plane crossing an internal cavity of a hollow organ and sets a visual line direction perpendicular to the projection plane in volume data representing a three-dimensional region including the hollow organ;
    a clip plane setting section that sets a clip plane crossing an internal cavity of the hollow organ;
    a dividing section that sets a portion in front in the visual line direction relative to the clip plane of the three-dimensional region as a visible region, and divides the field of view from the projection plane into a first field-of-view range in which the inside of the hollow organ is viewed and a second field-of-view range other than the first field-of-view range; and
    a projection image generation section that projects a portion within the first field-of-view range of the visible region onto the projection plane using a first template in which a relationship between a data value and opacity is defined so that an inner wall surface of the hollow organ is able to be drawn, to thereby acquire a first projection image in the first field-of-view range, projects a portion within the second field-of-view range of the visible region onto the projection plane using a second template in which the relationship between the data value and the opacity is defined so that a contact surface with the inner wall surface of the air region in the hollow organ is able to be drawn, to thereby acquire a second projection image in the second field-of-view range, and generates a projection image in the entire field of view in which the first projection image is connected to the second projection image.

* * * * *